United States Patent

Ahn et al.

Patent Number: 5,841,007
Date of Patent: Nov. 24, 1998

[54] PROCESS FOR MANUFACTURING 1,1,1,2-TETRAFLUOROETHANE

[75] Inventors: Byoung Sung Ahn; Young Soo Kwon; Kun You Park; Moon Jo Chung, all of Seoul, Rep. of Korea

[73] Assignee: Korea Institute of Science and Technology, Seoul, Rep. of Korea

[21] Appl. No.: 630,678

[22] Filed: Apr. 12, 1996

[51] Int. Cl.$^6$ .................................................. C07C 17/00
[52] U.S. Cl. ......................... 570/169; 570/165; 570/166; 570/167; 570/168
[58] Field of Search .................................. 570/169, 168, 570/167, 166, 165

[56] References Cited

U.S. PATENT DOCUMENTS

| | | |
|---|---|---|
| 3,728,405 | 4/1973 | Thoroughgood . |
| 3,787,331 | 1/1974 | Groppelli et al. . |
| 3,978,145 | 8/1976 | Knaak . |
| 3,992,325 | 11/1976 | Knaak . |
| 4,110,406 | 8/1978 | Anello et al. . |
| 4,158,675 | 6/1979 | Potter . |
| 5,057,634 | 10/1991 | Webster et al. . |
| 5,243,105 | 9/1993 | Scott et al. . |

FOREIGN PATENT DOCUMENTS

| | | |
|---|---|---|
| 0 449 614 | 10/1991 | European Pat. Off. . |
| 0 449 617 | 10/1991 | European Pat. Off. . |
| 1950 804 | 10/1970 | Germany . |
| 91 16657 | 11/1991 | Rep. of Korea . |
| WO 90/08755 | 8/1990 | WIPO . |
| WO 92/16480 | 10/1992 | WIPO . |
| WO 92/16481 | 10/1992 | WIPO . |

OTHER PUBLICATIONS

Chem Abst. 121: 86259 15 Mar. 1994.

*Primary Examiner*—Paul J. Killos
*Attorney, Agent, or Firm*—Oblon, Spivak, McClelland, Maier & Neustadt, P.C.

[57] ABSTRACT

The present invention relates to a process for manufacturing 1,1,1,2-tetrafluoroethane (HFC-134a) from trichloroethylene (TCE) and hydrogen fluoride (HF) by reacting the HCFC-133a with the HF to produce the HFC-134a and reacting the TCE with the HF to produce 1-choro-2,2,2-trifluoroethane (HCFC-133a), characterized by that a part of said HF is mixed with the mixture containing the HFC-134a and the remaining portion of said HF is fed with said TCE in portions to at least two sections of a reactor for producing said HCFC-133a. According the present process, the temperature change in the reactor for producing HCFC-133a is maintained within a narrow range over the whole reaction procedures, and the catalytic activity is well maintained. Further, the formation of by-products is considerably prevented and thus the productivity is remarkably enhanced.

4 Claims, 2 Drawing Sheets

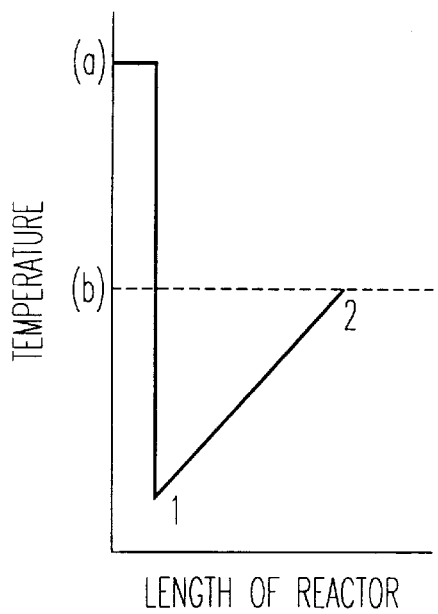
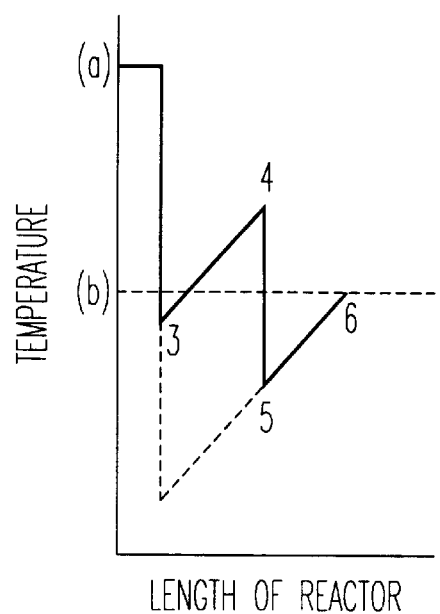
FIG. 3A  FIG. 3B
(a) TEMPERATURE OF EFFLUENT MIXTURE FROM REACTOR FOR PRODUCING HFC-134a
(b) UPPER LIMIT OF TEMPERATURE PREDETERMINED FOR PRODUCING HCFC-133a
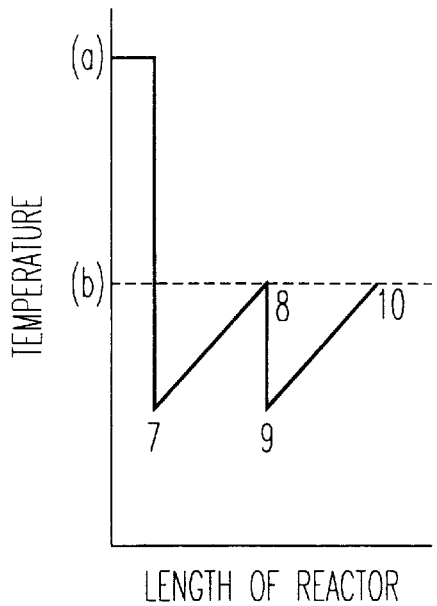
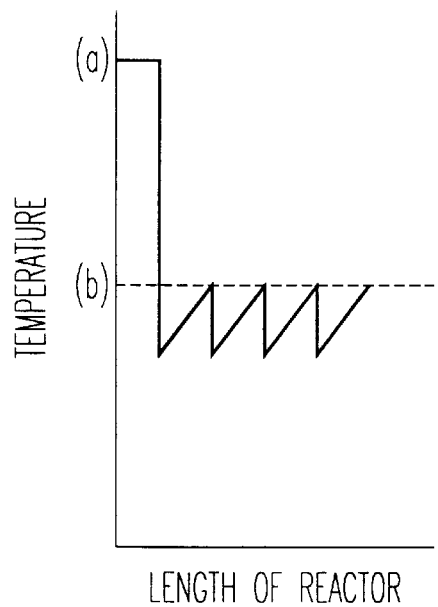
FIG. 3C  FIG. 3D

PROCESS FOR MANUFACTURING 1,1,1,2-TETRAFLUOROETHANE

BACKGROUND OF THE INVENTION

1. Field of the Invention

The present invention relates to a process for the manufacture of 1,1,1,2-tetrafluoroethane (HFC-134a, $CF_3CH_2F$). More specifically, the present invention relates to a process for manufacturing 1,1,1,2-tetrafluoroethane (HFC-134a) via an intermediate, 1-chloro-2,2,2-trifluoroethane (HCFC-133a), from trichloroethylene (TCE) and hydrogen fluoride (HF), wherein the temperature increase due to a heat of reaction is effectively controlled by feel the starting materials appropriately in portions to the manufacturing step of HCFC-133a.

2. Description of the Prior Art

CFC's such as dichlorodifluoromethane (CFC-12 or R-12) have been used as one of major refrigerants for various kinds of refrigeration systems. However, many studies and observations reveal that CFC's are one class of the main substances to deplete the stratospheric ozone. Among the several substitutes for CFC's, HFC-134a has been recognized as one of the most prospective substitutes for CFC's.

A number of processes for manufacturing HFC-134a are known depending on the starting materials employed. Among them a process using HF and TCE as starting materials is known as most favorable. In general, this process comprises the steps of: (1) reacting TCE with hydrogen fluoride to produce an intermediate HCFC-133a, and (2) reacting the intermediate with hydrogen fluoride to produce HFC-134a as follows:

$CCl_2=CHCl$ (TCE)+3HF→$CF_3CH_2Cl$ (HCFC-133a)+2HCl   (1)

$CF_3CH_2Cl$ (HCFC-133a)+HF→$CF_3CH_2F$ (HFC-134a)+HCl   (2)

In general, Cr-based catalysts such as, for example, chromic fluoride ($CrF_3$), and chromic oxyfluoride ($CrO_xF_y$) prepared by calcinating and fluorinating chronic hydroxide, chromic oxide, or chromic chloride are used for carrying out the above process. Additives such as cobalt and magnesium fluoride, or carriers such as alumina may be used, if appropriate.

International Publication No. WO90/08755 discloses a process wherein these two reaction steps are carried out in a single reaction system. This process, however, has a variety of problems that the catalytic activity decreases rapidly and that various by-products are produced due to the elevated temperature of the reaction mixture. Further, when oxygen is continuously introduced into the reactor for maintaining the catalytic activity, water is produced as a by-product. The water thus produced causes problems such as corrosion of the surfaces of the reaction vessels. In order to retard the deactivation rate of the catalyst, European Patent No. 0449 614 A2 proposes carrying out each reaction step in separate reaction vessel or different reaction zone.

In addition, for the purpose of enhancing the reaction productivity, European Patent No. 0449 617 A2 and Korean Unexamined Patent Publication No. 9 1-16657 disclose a process as depicted in FIG. 1 in which HCFC-133a is first reacted with an excess of hydrogen fluoride to produce HFC-134a according to Sequence (2) (reaction zone for producing HFC-134a; hereinafter to "HFC-134a reaction zone"), and the product which contains an excess of unreacted hydrogen fluoride is then mixed with TCE to produce HCFC-133a in accordance with Sequence (1) (reaction zone for producing HCFC-133a; hereinafter referred to "HCFC-133reaction zone"). Thereafter, HFC-134a and hydrogen chloride are removed from the product mixture and then the remaining mixture comprising HCFC-133a and hydrogen fluoride is recycled to the HFC-134a reaction zone. The another stark material, HF, is usually fed to the reactor in the HFC-134a reaction zone.

The reaction temperatures for these two steps vary with the catalysts employed therein. In a case whew a Cr-based catalyst is employed, he reaction step for preparing HFC-134a is carried out generally at the temperature ranging from 300° C. to 400° C., preferably from 340° C. to 380° C. The reaction step for HCFC-133a is carried out generally at the temperature ranging from 200° C. to 300° C., preferably from 250° C. to 300° C. Temperatures higher than 330° C. accelerate he deactivation rate of the catalyst and the formation of the by-products in the HCFC-133a reaction zone.

As mentioned above, the temperature of the HFC-134a reaction zone is high than that of the HCFC-133a reaction zone. Thus, it is necessary to cool the reaction product from the HFC-134a reaction zone for lowering the temperature thereof and then introduce the same into the HCFC-133a reaction zone. Although there is a difference depending upon the reaction conditions, when the temperature in the exit of the HFC-134a reaction zone is higher by 100° C. than in the inlet of the HCFC-133a reaction zone, heat of about 400 Mcal per ton of the HFC-134a produced should be removed, and thus an enormous and expensive heat exchanger is inevitable.

European Patent No. 0449 617 A2 suggests a partial use of the heat in the vaporization of another starting material, TCE. However, even by this process, the heat released from the HFC-134a reaction zone is not absorbed completely, and thus desirable cooling of the reaction product cannot be achieved.

The reaction step for preparing HCFC-133a is highly exothermic wherein about 30 kcal per mole of TCE are released as heat of reaction. Thus, the temperature of the reaction mixture increases rapidly during the reaction and temperature peak, called hot spot, may occur. The temperature peak accelerates the deactivation of the catalyst and the formation of the undesired by-products. In producing HCFC-133a, it is essential to choose the reaction condition, especially reaction temperature, in order to keep the temperature peak within the limit as well as to rise the reaction rate as far as possible. In this connection, there is known a method wherein the inner temperature of the reactor is controlled by a multiple tubular reactor and the wall of the reactor is cooled. However, such a multiple tubular reactor is expensive and the use of high corrosive fluid such as hydrogen fluoride requires much more expensive reactor made of special materials. Thus, this is not economical in view of the costs.

On the contrary, when a single tubular reactor is used for the reaction, the reaction temperature cannot be readily controlled only by cooling the wall of the reactor. Several methods have been proposed in that, for example, lowering sufficiently the temperature of reactant fluid in the inlet stage of the reaction, or introducing inert dilution gases into the reactor. However, when the temperature in the inlet stage is lowered, the reaction rate decreases and large reactor is required. When the dilution gas is introduced into the reactor so as to keep the temperature in the reactor within the limit, the reaction will also run slowly due to the declination of concentration of the reactants.

We, the inventors of the present invention, have intensively conducted a wide range of experiments in order to develop a process for preparing HCFC-133a in which a temperature of the reaction mixture can be effectively controlled in spite of the high exothermic reaction of manufacturing CFC-133a. As a result, we have discovered a method to maintain the reaction temperature within a narrow range over the entire reaction stages by feeding HF and TCE in portions to the reactor in view of the heat of reaction and the heats required in vaporization of HF and TCE, and could accomplish the present invention.

SUMMARY OF THE INVENTION

It is, therefore, an object of the invention to provide a process for manufacturing 1-chloro-2,2,2-trifluoroethane (HCFC-133a), an intermediate of 1,1,1,2-tetrafluoroethane (HFC-134a), in which the reaction temperature and the formation of by-products are effectively controlled.

It is an another object of the invention to provide a process for manufacturing HFC-134a with increased reaction conversion and with effective heat recovery.

Any additional objects of the invention will become apparent though reading the remainder of the specification.

BRIEF DESCRIPTION OF DRAWINGS

FIGS. 3A to 3D are graphs showing the temperature changes in the reactor for producing 1-chloro-2,2,2-trifluoroethane; when FIG. 3A indicates the temperature profile of the case where the reactant materials are fed in a portion to a reactor for producing HCFC-133a; FIG. 3B indicates the temperature profile of the case where the amount of the reaction materials are divided equally into in two portions and fed separately; FIG. 3C shows the temperature changes of the case that a part of HF is fed first to the reactor and then the feedstock comprising the remaining HF and TCE is divided equally into and fed in two portions; and FIG. 3D shows the temperature changes of the case that the starting material divided according to the invention and fed in portions to four places.

DETAILED DESCRIPTION OF THE INVENTION

Figure 1:
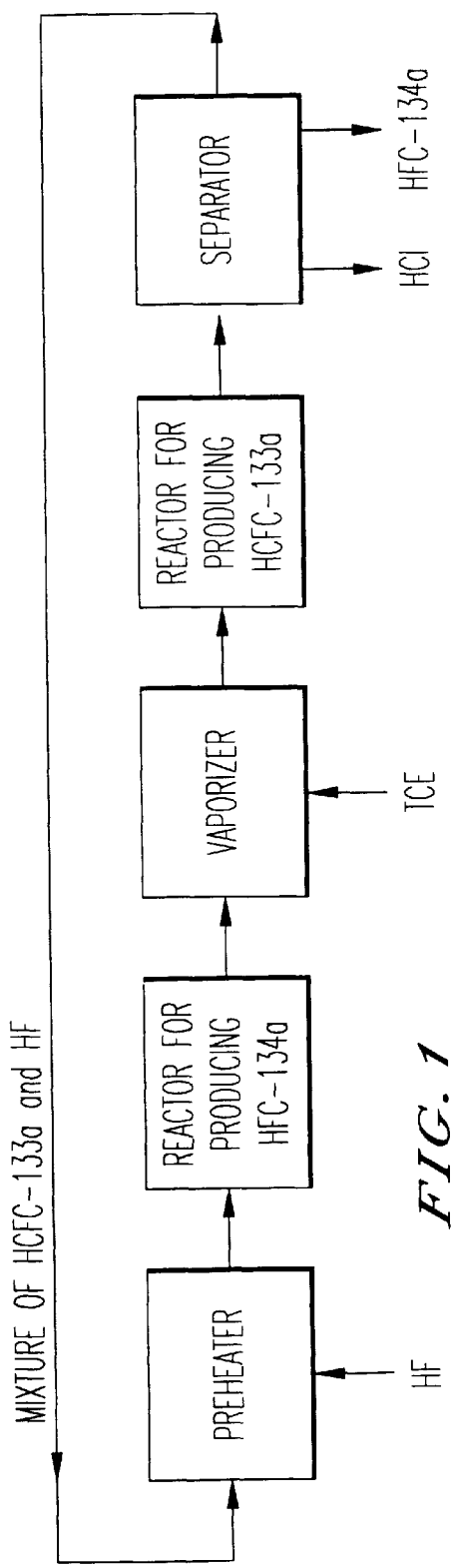
FIG. 1 is a schematic view showing a conventional process for producing 1,1,1,2-tetrafluoroethane.

According to the invention, a process is provided for manufacturing 1,1,1,2-tetrafluoroethane (HFC-134a) from trichloroethylene (TCE) and hydrogen fluoride (HF) by reacting TCE with hydrogen fluoride to produce 1-chloro-2,2,2-trifluoroethane (HCFC-133a) and reacting the resulting HCFC-133a with hydrogen fluoride to produce HFC-134a, characterized by reacting a part of the hydrogen fluoride with a product mixture containing the HFC-134a, and feeding the remaining part of the hydrogen fluoride with TCE in portions to at least two sections of a reactor for producing the HCFC-133a.

The process according to the invention is based on the heat and material balances as follows:

For the reaction for producing HCFC-133a about 30 kcal/mole of TCE is released as heat of reaction. It requires about 14 kcal/mole of TCE to vaporize and heat up TCE from ambient temperature to the reaction temperature of around 280° C., while about 9 kcal/mole of HF to vaporize and heat up hydrogen fluoride to the reaction temperature. Therefore, the heat of reaction released from 1 mole of TCE is almost equal to the heat to vaporize and heat up 1 mole of liquid TCE and about 1.8 moles of liquid HF. For example, in case where these two feeding materials at normal temperature in liquid state are fed at the above ratios to the HCFC-133a reaction zone maintained at 300° C. the mixture is cooled by a vaporization of the feeding materials and then, the temperature of the reaction zone will increase due to the heat of reaction. However, the temperature will not be over the point before the starting materials are introduced, namely 300° C. When amounts of the feeding materials to be introduced is reduced, the heat of reaction and the heat of vaporization are reduced concurrently. Therefore, the changes in the inner temperature of the reactor are suppressed.

Thus, the temperature changes due to the heat of reaction can be effectively controlled by premixing 2.2 moles of HF among total amounts (i.e., 4 moles) required for manufacturing HFC-134a with a product mixture from the HFC-134a reaction zone, and feeding the remaining 1.8 moles of HF appropriately in portions along with TCE to the suitable reaction sections in the reactor for producing HCFC133a. Since the temperature increases of the mixture are lessened by an increase in an amount of the mixture due to a supply of the feeding materials, it is practical that 2.3 to 2.6 moles of HF are mixed first with the product mixture from HFC-134a reaction zone, followed by feeding another 1.4 to 1.7 moles of HF in portions with TCE. In general, when liquid HF is fed at ambient temperature to the mixture in the amount of 2.3 to 2.6 moles per mole of TCE, the temperature of the mixture will be lowered by 70° C. to 80° C., though it may vary with the composition of the mixture. Thus, in case where the product mixture from the EFC-134a reaction zone has a temperature of about 370° C., the temperature in the HCFC-133a reaction zone may be controlled to lower than 300° C. and the temperature change in said reactor may be maintained within a range of 40° C. by the process according to the invention.

The calculation of the beat balance as stated herinbefore is very simplified. The precise heat balance may be calculated by taking into account of the reaction conditions, including the compositions of the products from the HEC-134a reaction zone, the conversion of the reaction step for producing HCFC-133a, and the heat transfer through a wall surface of the apparatus during the reaction and transportation.

The procedures for controlling the temperature changes in the process according to the invention will be explained in greater detail by referring to FIG. 2.

Figure 2:
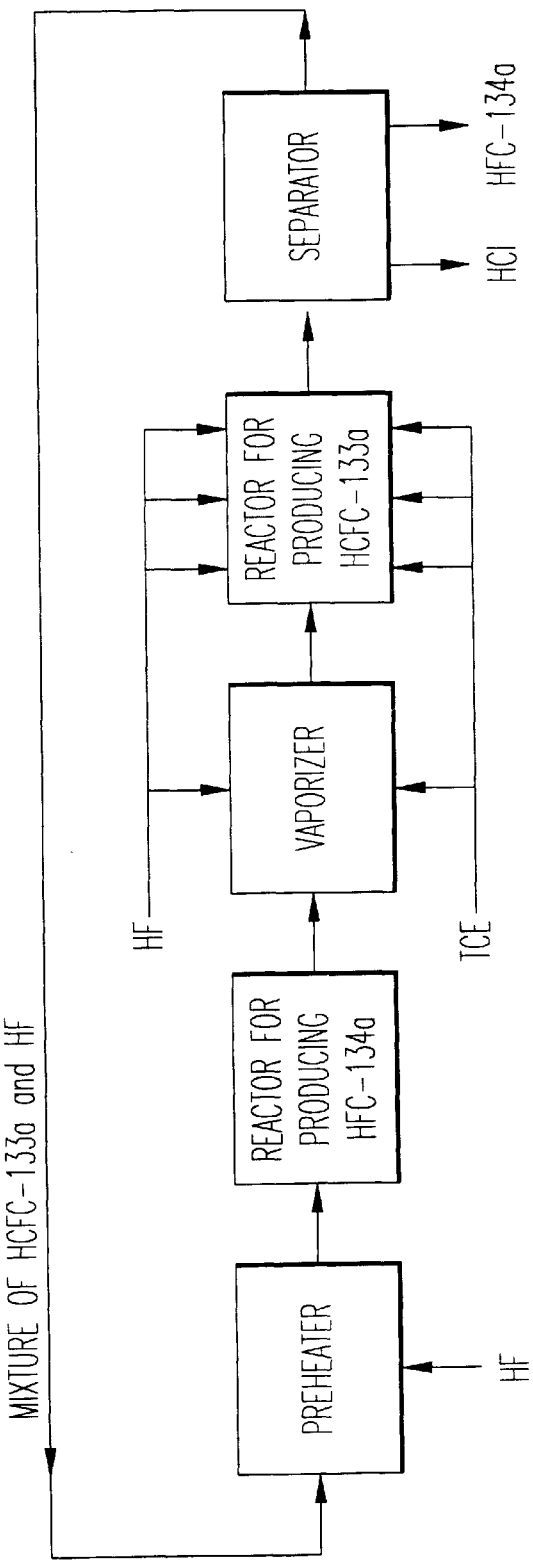
FIG. 2 is a schematic view showing a process for producing 1,1,1,2-tetrafluoroethane according to the invention.

FIG. 2 is a schematic view showing a process for manufacturing 1,1,1,2-tetrafluoroethane according to the invention. Part of the starting material HF is fed first to a vaporizer located between the HFC-134a reaction zone and the HCFC-133a reaction zone and contacted with the high-temperature product mixture from the HFC-134a reaction zone so that HF is vaporized concurrently with cooling of the product mixture. The amount of HF to be added may be determined by taking into account of the heat balance in the HCFC-133a reaction zone. It is preferred to add approximately 55% to 65% of the total amount of HF to be fed. The remaining HF is fed in portions along with another starting mail TCE. Preferably, HF and TCE are fed uniformly in portions by dividing this feedstock into two portions. As described hereinafter referring to FIG. 3, the higher number of dividing results in the narrower range of change in the temperature of the reactor. Thus, the dividing number can be suitably adjusted depending on the desired range of change in the reaction temperature, apparatus employed, and so forth.

According to an aspect of the invention, the first portion of the divided portions is fed along with an amount of HF to be introduced predominately to the vaporizer so as to contribute to the cooling of the product mixture from the HFC134a reaction zone.

As the feedstocks are transferred along the HCFC-133a reaction zone, the temperature in the reactor increases due to the heat of reaction released during the reaction and will approach to a predetermined upper limit at the point that most of the TCE is exhausted. At this point, if an additional amount of the starting materials are supplied, the mixture is cooled by vaporization and heating of the additional materials for a while and the temperature increases again due to the heat of reaction. These temperature declination and elevation are repeated several time until the producing HCFC-133a is completed.

The process according to the invention can be applied to any operation using a single reactor or two or more reactors if appropriate. When at least two reactors connected in series are used to the reaction step for producing HCFC-133a, the starting materials may be supplied to an individual vaporizer positioned prior to each reactor. In case where the single reactor is used, the starting materials may be fed in portions to a vaporizer positioned directly at the front of the reactor and the inner compartments in the reactor. Any suitable means can be installed to assist the vaporization and mixing in the reactor.

The advantages of the temperature control in the process according to the invention can be explained detail by referring to FIGS. 3. In order to facilitate the understanding of the invention, the temperature changes shown in FIGS. 3 are in the simplified cases where the reaction rate is not affected by the temperature and one of the starting materials, TCE, is completely reacted. However, additional cooling steps or addition of inert gases effective for the temperature control will be apparent to and can be readily made by those skilled in the art.

In FIGS. 3, the vertical axis indicates a temperature of the mixture in the HCFC-133a reaction zone, and the horizontal axis indicates a transverse position of the reactor. If two or more reactors connected in series are used, the horizontal axis indicates a total length of entire reactors employed. Point (a) means a temperature of the product mixture effused from the reactor for producing HFC-134a, and Point (b) represents an upper limit predetermined in the reaction for producing HCFC-133a. It is assumed that the mixture is not cooled by a heat loss during the reaction.

FIG. 3A indicates the temperature profile of the case where the starting materials are fed all at once to a reactor for producing HCFC-133a. The temperature of the mixture from the rector for producing HFC-134a is first declined to a point 1 when liquid staring materials are introduced into the vaporizer. However, the temperature is continuously elevated, until it approaches to a point 2 at the exit of the reactor, owing to the heat released during the reaction for producing HCFC-133a.

FIG. 3B indicates the temperature profile of the case where the starting materials are equally divided into and fed in two portions. When two reactors are used in series, the feedstocks are fed equally to each vaporizer positioned prior to the individual reactor. In case of the single reactor, the materials are supplied equally to the vaporizer prior to the reactor and the middle of the reactor. As shown in FIG. 3B, the mixture from the reactor for producing HFC134a is cooled to a point 3 when it is mixed with a half of the total amount of the starting materials. Then, the temperature is elevated to a point 4 due to a heat released during the reaction. Similarly, the mixture is mixed with another half of the starting materials to cool to a point 5, and then the temperature is elevated to a point 6 due to a heat released during the reaction. If the whole amount of TCE added participates in the reaction, the temperature point 6 will theoretically be identical to the point 2 in FIG. 3A.

As explained in the above, in case that the starting materials are equally divided and simply fed to the reactor in portions, the temperature of the mixture during the reaction exceeds the upper limit of the temperature. To avoid this, in the process according to the invention, a part of HF is fed first to the reactor and then the feedstock comprising the remaining HF and TCE is divided equally into and fed in two portions to the HCFC-133a reaction zone.

In this case, the temperature changes can be effectively controlled by feeding the first portion of the feedstocks with the part of HF to be fed predominantly and introducing the remaining portion of the feedstocks into the middle of the reactor. When the starting materials are fed in this manner, the reactant mixture is mixed with the part of HF to be fed first and a half of the remaining feedstocks to cool to a point 7 as depicted in FIG. 3C. Then, the temperature is elevated to a point 8 during the reaction. Thereafter, the reactant is mixed with another half of the feedstocks to cool to a point 9, and then the temperature is elevated to a point 10 due to a heat released during the reaction.

FIG. 3D shows the temperature changes of the case that the starting materials are fed in portions to four places. The higher number of dividing the amount of the starting materials will result in the narrower range of changes in the temperature of the reactor.

When the starting materials are fed in port to two places, the range of the temperature changes will be about a half of that in feeding all at once. This will decrease to around a quarter when the starting materials are fed in portions to four places. In practice, when the whole amount of the starting materials are fed in a portion to a vaporizer positioned dry in the front of the reactor, the range of the temperature changes in the reactor for producing HCFC-133a is around 65° C. On the contrary, this is declined to about 35° C. when the starting materials are fed to two places according to the invention, while about 18° C. when fed to four places.

According to the present process, the reaction steps are carried out effectively and thus the conversion is also enhanced. This is because the temperature, with which the reaction rate is varied, can be maintained as high as possible below the predetermined limit.

As explained above, according to the process of the invention, the reaction steps can be carried out effectively at the temperature within a predetermined upper limit while maintaining the temperature changes in a narrow range even though further cooling or addition of inert gases is not included therein.

DESCRIPTION OF THE PREFERRED EMBODIMENTS

The present invention will be illustrated in greater detail by way of the following examples. The examples are presented for illustration purpose only and should not be construed as limiting the invention, which is properly delineated in the claims. Various other modifications will be apparent to and can be readily made by those skilled in the art without departing from the scope and spirit of the invention.

In the examples, the following apparatus is employed: a single tubular reactor having a diameter of 5 inches (about 12.7 cm) and a length of 90 cm was used for the HFC-134a reaction zone. The reactor was filled with 6.8 kg of catalysts (catalyst length: 60 cm).

The same single tubular reactor as that used for the HFC-134a reaction zone was employed for the HCFC-133a reaction zone. But the inner space of the reactor was divided by four catalytic layers having a length of 10 cm each, and vaporization layers having a length of 5 cm were interposed between the catalytic layers. Each catalytic layer was charged with 1.1 kg of catalysts, and thermocouple thermometers were installed in the front and the rear of each catalytic layer. Vaporization layers were filled with Raschig rings and the starting materials, HF and TCE, were supplied to the middle of each of the vaporization layers.

A preheater for vaporizing and preheating the reactant mixture was located in the front of the reactor. Also a vaporizer filled with Raschig rings was positioned between the two reactors.

The catalysts used for producing HFC-134a and HCFC-133a were Cr-based catalysts. The apparatus and interiors thereof were made of Inconel 600. The reactors and vaporizers were insulated by a refractory heat insulating material to suppress the heat loss.

EXAMPLE 1

In this example, the reaction step for producing HCFC-133a was carried out by first feeding 60% of HF, and then dividing the rest materials (HF and TCE) into two portions followed by feeding separately them to the reactor.

A mixed solution of HF and HCFC-133a in a molar ratio of 7.5:1 was passed through a preheater at a flow rate of 3,580 g/hr to heat to 375° C., and then fed to the reactor for producing HFC-134a. The reaction temperature was maintained at 370° C. and the reaction pressure was under 7 kg/cm$^2$. Average conversion of HCFC-133a in the reaction for producing HFC-134a was found to be 25.5%, and selectivity to HFC-134a to be above 97%.

The product mixture was transferred to the vaporizer and mixed with HF at a flow rate of 213 g/hr (10.66 gmol/hr) and TCE at a flow rate of 219 g/hr (1.67 gmol/hr) in the vaporizer. These correspond to 80% (60%+a half of the remainder) of the total amount of HF and 50% of the total amount of TCE. The mixture at 370° C. was cooled to 261° C. after being mixed with the materials, and the temperature was elevated to 298° C. due a heat of reaction, while the mixture was passed through the continuous two catalytic layers in the reactor for producing HCFC-133a.

The remaining HF and TCE were introduced into the third vaporization layer at flow rates of 54 g/hr (2.67 gmol/hr) and 219 g/hr (1.67 gmol/hr), respectively. The temperature was declined to 263° C. and then continued to increase until it reached 296° C. while passing the mixture through two catalytic layers.

The temperature change in the reactor for producing HCFC-133a was in the range of from 33° C. to 37° C. The final conversion of TCE was found to be 95% and the catalytic activity was maintained even after a 60 hour continuous operation.

EXAMPLE 2

In this example, the reaction for preparing HCFC-133a was carried out by first feeding 62.7% of HF and then dividing the rest materials into four portions followed by feeding them to the reactor.

HFC-134a mixture was produced at the same flow rates and under the same reaction conditions, as described in Example 1. The mixture thus prepared was transferred to the vaporizer and mixed with HF at a flow rate of 192 g/hr (9.6 gmol/hr) and TCE at a flow rate of 109 g/hr (0.83 gmol/hr) in the vaporizer. These correspond to 72% (62.7%+a quarter of the remainder) of the total amount of HF and 25% of the total amount of TCE. The reactant mixture at 370° C. was cooled to 280° C. after mixed with the materials, and the temperature was elevated to 299° C. after the mixture was passed through the first catalytic layer. HF and TCE were fed to the vaporization layer located prior to the second catalytic layer at flow rates of 25 g/hr (1.24 gmol/hr) and 109 g/hr (0.83 gmol/hr), respectively. These correspond to 9.3% (a quart of the remainder) of the total amount of H and 25% of the total amount of TCE. The temperatures in the front and the rear of the second catyalytic layer were 279° C. and 297° C., respectively. Similarly, two portions of the starting materials were fed to the third and fourth vaporization layers. The temperatures in the front and the rear of these catalytic layers were 278° C. and 297° C., and 278° C. and 297° C., respectively.

The temperature change in the reactor for producing HCFC-133a was in the range of from 18° C. to 19° C. The final conversion of TCE was found to be above 97% and the catalytic activity was maintained even after a 70 hour continuous operation.

Comparative Example 1

In this example, the whole amount of HB and TCE were fed at once to the vaporizer to carry out the reaction for producing HCFC-133a.

HFC-134a was produced at the same flow rates and under the same reaction conditions, as described in Example 1. The mixture thus prepared was transferred to the vaporizer and mixed with HF at a flow rate of 267 g/hr (13.4 gmol/hr) and TCE at a flow rate of 438 g/hr (3.3 gmol/hr) in the vaporizer. The mixture at 370° C. was cooled to 225° C. after being mixed with the materials, and the temperatures was elevated to 289° C. when passing the mixture through all the catalytic layers.

The temperature change in the reactor for producing HCFC-133a was 64° C. The final conversion of TCE was found to be 92% and the catalyst was deactivated after a 40 hour continuous operation.

What is claimed is:

1. A process for manufacturing 1,1,1,2-tetrafluoroethane comprising:

i) introducing hydrogen fluoride and 1,1,1,2-tetrafluoroethane to a reactor comprising a catalyst; and reacting hydrogen fluoride and trichloroethylene in said reactor, to form 1-chloro-2,2,2-trifluoroethane, wherein said hydrogen fluoride and said trichloroethylene are divided into at least two portions, and wherein at least one of said portions is introduced into said reactor downstream of an inlet for said hydrogen fluoride and 1,1,1,2-tetrafluoroethane, and ii) reacting 1-chloro-2,2,2-trifluoroethane with hydrogen fluoride to produce 1,1,1,2-tetrafluoroethane.

2. A process for the manufacturing of 1-chloro-2,2,2-trifluoroethane comprising:

introducing hydrogen fluoride and 1,1,1,2-tetrafluoroethane to a reactor comprising a catalyst; and reacting hydrogen fluoride and trichloroethylene in said reactor, to form 1-chloro-2,2,2-trifluoroethane, wherein said hydrogen fluoride and said trichloroethylene are divided into at least two portions, and wherein at least one of said portions is introduced into said reactor downstream of an inlet for said hydrogen fluoride and 1,1,1,2-tetrafluoroethane.

3. The process according to claim 5, wherein 55 to 65% of a total amount of said hydrogen fluoride is added to said 1,1,1,2-tetrafluoroethane before being introduced into the reactor for producing said 1-chloro-2,2,2-trifluoroethane and a feedstock comprising the remaining said HF and said TCE is divided equally and fed in portions to at least two sections of the reactor.

4. The process according to claim 1, wherein the upper limit of the temperature in the reactor producing said 1-chloro-2,2,2-trifluoroethane is maintained at below 300° C., and the temperature change in said reactor is maintained within a range of 40° C.

* * * * *